US006477400B1

(12) United States Patent
Barrick

(10) Patent No.: US 6,477,400 B1
(45) Date of Patent: Nov. 5, 2002

(54) FLUOROSCOPIC IMAGE GUIDED ORTHOPAEDIC SURGERY SYSTEM WITH INTRAOPERATIVE REGISTRATION

(75) Inventor: Earl Frederick Barrick, McLean, VA (US)

(73) Assignee: Sofamor Danek Holdings, Inc., Memphis, TN (US)

( * ) Notice: Subject to any disclaimer, the term of this patent is extended or adjusted under 35 U.S.C. 154(b) by 0 days.

(21) Appl. No.: 09/376,712

(22) Filed: Aug. 16, 1999

Related U.S. Application Data

(60) Provisional application No. 60/097,742, filed on Aug. 24, 1998, and provisional application No. 60/097,183, filed on Aug. 20, 1998.

(51) Int. Cl.[7] ............................................... A61B 5/00
(52) U.S. Cl. ....................... 600/426; 600/427; 606/130
(58) Field of Search ............................... 600/407, 426, 600/427, 429; 606/130, 97; 378/20, 205, 206, 207, 62

(56) References Cited

U.S. PATENT DOCUMENTS

| | | |
|---|---|---|
| 1,576,781 A | 3/1926 | Philips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Zehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,294,083 A | 12/1966 | Alderson |
| 3,367,326 A | 2/1968 | Frazier |
| 3,577,160 A | 5/1971 | White |

(List continued on next page.)

FOREIGN PATENT DOCUMENTS

| | | | |
|---|---|---|---|
| DE | 3042343 | 6/1982 | |
| EP | 964149 | 3/1975 | ............ A61B/8/14 |

(List continued on next page.)

OTHER PUBLICATIONS

Adams, L., Knepper, A., Krybus, W., Meyer–Ebrecht, D., Pfeifer, G., Ruger, R., Witte, M., *Aide au Reperage Tridimensionnel pour la Chirurgie de la Base du Crane*, Innov. Tech. Biol. Med., vol. 13, No. 4, 1992, pp. 409–424.

Barrick, E.F., "Journal of Orthopaedic Trauma: Distal Locking Screw Insertion Using a Cannulated Drill Bit: Technical Note," Raven Press, vol. 7, No. 3, 1993, pp. 248–251.

Barrick et al., "Prophylactic Intramedullary Fixation of the Tiba for Stress Fracture in a Professional Athlete," *Journal of Orthopaedic Trauma*, vol. 6, No. 2, pp. 241–244 (1992).

(List continued on next page.)

*Primary Examiner*—Ruth S. Smith
(74) *Attorney, Agent, or Firm*—Harness, Dickey & Pierce, P.L.C.

(57) ABSTRACT

A fluoroscopic image guided surgery system, comprising a C-arm fluoroscope for obtaining fluoroscopic images of an object bone, the C-arm fluoroscope including at least one set of emitters; a reference bar capable of attaching to an object bone, the reference bar including emitters; a surgical instrument for performing an operation, the instrument including emitters; a digitizer system in communication with the at least one set of emitters of the C-arm fluoroscope, the emitters of the reference bar, and the emitters of the surgical instrument so that the digitizer system can determine a position of each of the C-arm fluoroscope, the reference bar, and the surgical instrument; and a single fiducial marker for attachment to an object bone, the single fiducial marker being visible in the fluoroscopic images for determining a position of an object bone relative to the digitizer system.

23 Claims, 3 Drawing Sheets

U.S. PATENT DOCUMENTS

| | | |
|---|---|---|
| 3,702,935 A | 11/1972 | Carey et al. |
| 3,704,707 A | 12/1972 | Halloran |
| 3,941,127 A | 3/1976 | Froning |
| 4,037,592 A | 7/1977 | Kronner |
| 4,117,337 A | 9/1978 | Staats |
| 4,202,349 A | 5/1980 | Jones |
| 4,358,856 A | 11/1982 | Stivender et al. |
| 4,403,321 A | 9/1983 | DiMarco |
| 4,418,422 A | 11/1983 | Richter et al. |
| 4,485,815 A | 12/1984 | Amplatz |
| 4,543,959 A | 10/1985 | Sepponen |
| 4,621,628 A | 11/1986 | Blundermann |
| 4,625,718 A | 12/1986 | Olerud et al. |
| 4,651,732 A | 3/1987 | Frederick |
| 4,653,509 A | 3/1987 | Oloff et al. |
| 4,706,665 A | 11/1987 | Gouda |
| 4,722,056 A | 1/1988 | Robert et al. |
| 4,722,336 A | 2/1988 | Kim et al. |
| 4,727,565 A | 2/1988 | Ericson |
| 4,737,921 A | 4/1988 | Goldwasser et al. |
| 4,750,487 A | 6/1988 | Zanetti |
| 4,771,787 A | 9/1988 | Wurster et al. |
| 4,791,934 A | 12/1988 | Brunnett |
| 4,797,907 A | 1/1989 | Anderton |
| 4,803,976 A | 2/1989 | Frigg et al. |
| 4,821,206 A | 4/1989 | Arora |
| 4,991,579 A | 2/1991 | Allen |
| 5,013,317 A | 5/1991 | Cole et al. |
| 5,027,818 A | 7/1991 | Bova et al. |
| 5,030,222 A | 7/1991 | Calandruccio et al. |
| 5,031,203 A | 7/1991 | Trecha |
| 5,059,789 A | 10/1991 | Salcudean |
| 5,079,699 A | 1/1992 | Tuy et al. |
| 5,094,241 A | 3/1992 | Allen |
| 5,097,839 A | 3/1992 | Allen |
| 5,107,843 A | 4/1992 | Aarnio et al. |
| 5,119,817 A | 6/1992 | Allen |
| 5,142,930 A | 9/1992 | Allen et al. |
| 5,154,717 A * | 10/1992 | Matsen, III et al. .......... 606/53 |
| 5,178,164 A | 1/1993 | Allen |
| 5,178,621 A | 1/1993 | Cook et al. |
| 5,186,174 A | 2/1993 | Schlondorff et al. |
| 5,198,877 A | 3/1993 | Schulz |
| 5,211,164 A | 5/1993 | Allen |
| 5,212,720 A | 5/1993 | Landi et al. |
| 5,219,351 A | 6/1993 | Teubner et al. |
| 5,249,581 A | 10/1993 | Horbal et al. |
| 5,251,127 A | 10/1993 | Raab |
| 5,295,483 A | 3/1994 | Nowacki et al. |
| 5,305,203 A | 4/1994 | Raab |
| 5,309,913 A | 5/1994 | Kormos et al. |
| 5,320,111 A | 6/1994 | Livingston |
| 5,333,168 A | 7/1994 | Fernandes et al. |
| 5,368,030 A | 11/1994 | Zinreich et al. |
| 5,383,454 A | 1/1995 | Bucholz |
| 5,389,101 A | 2/1995 | Heilbrun et al. |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,426,683 A | 6/1995 | O'Farrell, Jr. et al. |
| 5,426,687 A | 6/1995 | Goodall et al. |
| 5,427,097 A | 6/1995 | Depp |
| RE35,025 E | 8/1995 | Anderton |
| 5,446,548 A | 8/1995 | Gerig et al. |
| 5,447,154 A | 9/1995 | Cinquin et al. |
| 5,478,341 A | 12/1995 | Cook et al. |
| 5,478,343 A | 12/1995 | Ritter |
| 5,483,961 A | 1/1996 | Kelly et al. |
| 5,490,196 A | 2/1996 | Rudich et al. |
| 5,494,034 A | 2/1996 | Schlöndorff et al. |
| 5,503,416 A | 4/1996 | Aoki et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,568,809 A | 10/1996 | Ben-haim |
| 5,572,999 A | 11/1996 | Funda et al. |
| 5,583,909 A | 12/1996 | Hanover |
| 5,588,430 A | 12/1996 | Bova et al. |
| 5,596,228 A | 1/1997 | Anderton et al. |
| 5,603,318 A | 2/1997 | Heilbrun et al. |
| 5,617,462 A | 4/1997 | Spratt |
| 5,617,857 A | 4/1997 | Chader et al. |
| 5,619,261 A | 4/1997 | Anderton |
| 5,622,170 A | 4/1997 | Schulz |
| 5,627,873 A | 5/1997 | Hanover et al. |
| 5,630,431 A | 5/1997 | Taylor |
| 5,638,819 A | 6/1997 | Manwaring et al. |
| 5,642,395 A | 6/1997 | Anderton et al. |
| 5,647,361 A | 7/1997 | Damadian |
| 5,662,111 A | 9/1997 | Cosman |
| 5,676,673 A | 10/1997 | Ferre et al. |
| 5,682,886 A | 11/1997 | Delp et al. |
| 5,690,108 A | 11/1997 | Chakerers |
| 5,695,500 A | 12/1997 | Taylor et al. |
| 5,695,501 A | 12/1997 | Carol et al. |
| 5,711,299 A | 1/1998 | Manwaring et al. |
| 5,748,767 A | 5/1998 | Raab |
| 5,749,362 A | 5/1998 | Funda et al. |
| 5,755,725 A | 5/1998 | Druais |
| 5,769,789 A | 6/1998 | Wang et al. |
| 5,769,861 A | 6/1998 | Vilsmeier |
| 5,772,594 A | 6/1998 | Barrick |
| 5,795,294 A | 8/1998 | Luber et al. |
| 5,799,055 A | 8/1998 | Peshkin et al. |
| 5,800,535 A | 9/1998 | Howard, III |
| 5,802,719 A | 9/1998 | O'Farrell, Jr. et al. |
| 5,823,958 A | 10/1998 | Truppe |
| 5,828,725 A | 10/1998 | Levinson |
| 5,833,608 A | 11/1998 | Acker |
| 5,834,759 A | 11/1998 | Glossop |
| 5,836,954 A | 11/1998 | Heilbrun et al. |
| 5,848,967 A | 12/1998 | Cosman |
| 5,851,183 A | 12/1998 | Bucholz |
| 5,868,675 A | 2/1999 | Henrion et al. |
| 5,871,445 A | 2/1999 | Bucholz |
| 5,871,487 A | 2/1999 | Warner et al. |
| 5,891,034 A | 4/1999 | Bucholz |
| 5,891,157 A | 4/1999 | Day et al. |
| 5,904,691 A | 5/1999 | Barnett et al. |
| 5,920,395 A | 7/1999 | Schulz |
| 5,921,992 A | 7/1999 | Costales et al. |
| 5,951,475 A * | 9/1999 | Gueziec et al. ............. 600/425 |
| 6,006,127 A * | 12/1999 | Van Der Brug et al. .... 600/427 |
| 6,021,343 A * | 2/2000 | Foley et al. ................. 600/429 |
| 6,036,696 A * | 3/2000 | Lambrecht et al. ........... 606/97 |
| 6,050,724 A * | 4/2000 | Schmitz et al. ............. 378/205 |
| 6,157,853 A * | 12/2000 | Blume et al. ................ 600/426 |
| 6,167,145 A * | 12/2000 | Foley et al. ................. 600/426 |
| 6,314,310 B1 * | 11/2001 | Ben-Haim et al. .......... 600/424 |

FOREIGN PATENT DOCUMENTS

| | | | |
|---|---|---|---|
| EP | 350996 | 1/1990 | |
| EP | 0 581 704 A1 | 7/1993 | ............ A61B/8/14 |
| FR | 79 04241 | 2/1979 | ........... A61B/17/18 |
| WO | WO 88/09151 | 12/1988 | ........... A61B/19/00 |
| WO | WO 91/03982 | 4/1991 | |
| WO | WO 91/04711 | 4/1991 | ........... A61B/19/00 |
| WO | WO 91/07726 | 5/1991 | ........... G06F/15/72 |
| WO | WO 92/06645 | 4/1992 | ........... A61B/19/00 |

| | | | | |
|---|---|---|---|---|
| WO | WO 94/23647 | 10/1994 | ............ | A61B/5/05 |
| WO | WO 94/24933 | 11/1994 | ............ | A61B/5/05 |
| WO | WO 96/11624 | 4/1996 | | |
| WO | WO 98/38908 | 9/1998 | ............ | A61B/5/00 |

OTHER PUBLICATIONS

Barrick et al., "Technical Difficulties with the Brooker–Wills Nail in Acute Fractures of the Femur," *Journal of Orthopaedic Trauma*, vol. 4, No. 2, pp. 144–150 (1990).

Batnitzky, S., Price, H.I., Lee, K.R., Cook, P.N., Cook, L.T., Fritz, S.L., Dwyer, S.J., Watts, C., *Three–Dimensional Computer Reconstructions of Brain Lesions from Surface Contours Provided by Computed Tomography*: A Prospectus, Neurosurgery, vol. 11, No. 1, Part 1, 1982, pp. 73–84.

Brack, C., et al., "Accurate X–ray Based Navigation in Computer–Assisted Orthopedic Surgery," CAR '98, pp. 716–722.

Bouazza–Marouf et al., "Robotic–Assisted Internatl Fixation of Femoral Fractures," *IMECHE.*, pp. 51–58 (1995).

Champleboux, G., *Utilisation de Fonctions Splines pour la Mise au Point D'un Capteur Tridimensionnel sans Contact*, Quelques Applications Medicales, Jul. 1991.

Cinquin, P., et al., "Computer Assisted Medical Interventions," IEEE Engineering in Medicine and Biology, May/Jun. 1995, pp. 254–263.

Cinquin, P., Lavallee, S., Demongeot, J., *Computer Assisted Medical Interventions*, International Advanced Robotics Programme, Sep. 1989, pp. 63–65.

Clarysse, P., Gibon, D., Rousseau, J., Blond, S., Vasseur, C., Marchandise, X., *A Computer–Assisted System for 3–D Frameless Localization in Stereotaxic MRI*, IEEE Transactions on Medical Imaging, vol. 10, No. 4, Dec. 1991, pp. 523–529.

Colchester, A.C.F., Hawkes, D.J., *Information Processing in Medical Imaging*, Lecture Notes in Computer Science, $12^{th}$ International Conference, IPMI, Jul. 1991, pp. 136–141.

Feldmar, J., et al., "3D–2D Projective Registration of Free–Form Curves and Surfaces," Rapport de recherche (Inria Sophia Antipolis), 1994, pp. 1–44.

Foley, J.D., Van Dam, A., *Fundamentals of Interactive Computer Graphics*, The Systems Programming Series, Chapter 7, Jul. 1984, pp. 245–266.

Foley, K.T., Smith, K.R., Bucholz, R.D., *Image–guided Intraoperative Spinal Localization*, Intraoperative Neuroprotection, Chapter 19, 1996, pp. 325–340.

Gildenberg, P.L., Kaufman, H.H., Murthy, K.S., *Calculation of Stereotactic Coordinates from the Computed Tomographic Scan*, Neurosurgery, vol. 10, No. 5, May 1982, pp. 580–586.

Gonzalez, R.C., *Digital Image Fundamentals*, Digital Image Processing, Second Edition, 1987, pp. 52–54.

Gottesfeld Brown, L.M., et al., "Registration of Planar Film Radiographs with Computer Tomography," Proceedings of MMBIA, Jun. '96, pp. 42–51.

Guéziec, A.P., et al., "Registration of Computer Tomography Data to a Surgical Robot Using Fluorscopy: A Feasibility Study," Computer Science/Mathematics, Sep. 27, 1996, 6 pages.

Hamadeh, A., et al., "Towards Automatic Registration Between CT and X–ray Images: Cooperation Between 3D/2D Registration and 2D Edge Detection," MRCAS '95, pp. 39–46.

Hamadeh, A., et al., "Kinematic Study of Lumbar Spine Using Functional Radiographies and 3D/2D Registration," TIMC UMR 5525—IMAG.

Hamadeh, A., et al., "Automated 3–Dimensional Computer Tomographic and Fluoroscopic Image Registration," Computer Aided Surgery (1998), 3:11–19.

Hatch, J.F., *Reference–Display System for the Integration of CT Scanning and the Operating Microscope*, Thesis, Thayer School of Engineering, Oct. 1984, pp. 1–189.

Henderson, J.M., Smith, K.R., Bucholz, R.D., *An Accurrate and Ergonomic Method of Registration for Image–guided Neurosurgery*, Computerized Medical Imaging and Graphics, vol. 18, No. 4, Jul.–Aug. 1994, pp. 273–277.

Hoerenz, P., *The Operating Microscrope I. Optical Principles, Illumination Systems, and Support Systems*, Journal of Microsurgery, vol. 1, 1980, pp. 364–369.

Hofstetter, R., et al., "Fluoroscopy Based Surgical Navigation—Concept and Clinical Applications," Computer Assisted Radiology and Surgery, 1997, pp. 956–960.

Hounsfield, G.N., *Computerized transverse axial scanning (tomography)*: Part I. Description of system, British Journal of Radiology, vol. 46, No. 552, Dec. 1973, pp. 1016–1022.

Jacques, S., Shelden, C.H., McCann, G.D., *A Computerized Microstereotactic Method to Approach, 3–Dimensionally Reconstruct, Remove and Adjuvantly Treat Small CNS Lesions*, Applied Neurophysiology, vol. 43, 1980, pp. 176–182.

Jacques, S., Shelden, C.H., McCann, G.D., Freshwater, D.B., Rand, R., *Computerized three–dimensional stereotaxic removal of small central nervous system lesion in patients*, J. Neurosurg., vol. 53, Dec. 1980, pp. 816–820.

Joskowicz, L., et al., "Computer–Aided Image–Guided Bone Fracture Surgery: Concept and Implementation," CAR '98, pp. 710–715.

Kelly, P.J., Kall, B., Goerss, S., Alker, G.J., Jr., *Precision Resection of Intra–Axial CNS Lesions by CT–Based Stereotactic Craniotomy and Computer Monitored $CO_2$ Laser*, Acta Neurochirurgica, vol. 68, 1983, pp. 1–9.

Lavalle, S., et al., "Computer Assisted Spine Surgery: A Technique For Accurate Transpedicular Screw Fixation Using CT Data and a 3–D Optical Localizer," TIMC, Faculte de Medecine de Grenoble.

Lavallee, S., et al., "Image guided operating robot: a clinical application in stereotactic neurosurgery," Proceedings of the 1992 IEEE Internation Conference on Robotics and Automation, May 1992, pp. 618–624.

Lavallée, S., Brunie, L., Mazier, B., Cinquin, P., *Matching of Medical Images for Computed and Robot Assisted Surgery*, IEEE EMBS, Orlando, 1991.

Lavallée, S., Cinquin, P., Demongeot, J., Benabid, A.L., Marque, I., Djaid, M., *Computer Assisted Driving of a Needle into the Brain*, Proceedings of the International Symposium: CAR 89, pp. 416–420.

Lavallée, S., *A New System for Computer Assisted Neurosurgery*, IEEE Engineering in Medicine & Biology Society $11^{th}$ Annual International Conference, 1989, pp. 0926–0927.

Lavallée, S., *VI Adaptation de la Methodologie a Quelques Applications Cliniques*, Chapitre VI, pp. 133–148.

Lavallée, S., Szeliski, R., Brunie, L., *Matching 3–D Smooth Surfaces with Their 2–D Projections using 3–D Distance Maps*, SPIE, vol. 1570, Geometric Methods in Computer Vision, 1991, pp. 322–336.

Lavellé S., Cinquin, P., Demongeot, J., Benabid, A.L., Marque, I., Djaid, M., *Computer Assisted Interventionist Imaging: The Instance of Stereotactic Brain Surgery*, North-Holland MEDINFO 89, Part 1, 1989, pp. 613–617.

Leksell, L., Jernberg, B., *Stereotaxis and Tomography—A Technical Note*, ACTA Neurochirurgica, vol. 52, 1980, pp. 1–7.

Lemieux, L., et al., "A Patient–to–Computer–Tomography Image Registration Method Based on Digitally Reconstructed Radiographs," Med. Phys. 21 (11), Nov. 1994, pp. 1749–1760.

Levin, D.N., Hu, X., Tan, K.K., Galhotra, S., Pelizzari, C.A., Chen, G.T.Y., Beck, R.N., Chen, C., Cooper, M.D., Mullan, J.F., Hekmatpanah, J., Spire, J., *The Brain: Integrated Three–dimensional Display of MR and PET Images*, Radiology, vol. 172, No. 3, Sep. 1989, pp. 783–789.

Mazier, B., Lavallée, S., Cinquin, P., *Chirurgie de la Colonne Vertebrale Assistee par Ordinateur: Appication au Vissage Pediculaire*, Innov. Tech. Biol. Med., vol. 11, No. 5, 1990, pp. 559–566.

Mazier, B., Lavallee, S., Cinquin, P., *Computer Assisted Interventionist Imaging: Application to the Vertebral Column Surgery*, Annual International Conference of the IEEE Engineering in Medicine and Biology Society, vol. 12, No. 1, 1990, pp. 0430–0431.

PCT International Search Report, PCT/US99/14565, Oct. 20, 1999.

Pelizzari, C.A., Chen, G.T.Y., Spelbring, D.R., Weichselbaum, R.R., Chen, C., *Accurate Three–Dimensional Registration of CT, PET, and/or MR Images of the Brain*, Journal of Computer Assisted Tomography, Jan./Feb. 1989, pp. 20–26.

Pelizzari, C.A., Chen, G.T.Y., Halpern, H., Chen, C.T., Cooper, M.D., *No. 528—Three Dimensional Correlation of PET, CT and MRI Images*, The Journal of Nuclear Medicine, vol. 28, No. 4, Apr. 1987, p. 682.

Phillips, R., et al., "Image Guided Orthopaedic Surgery Design and Analysis," Trans Inst MC, vol. 17, No. 5, 1995, pp. 251–264.

Potamianos, P., et al., "Intra–Operative Imaging Guidance for Keyhole Surgery Mehtodology and Calibration," First International Symposium on Medical Robotics and Computer Assisted Surgery, Sep. 22–24, 1994, pp. 98–104.

Reinhardt, H.F., Landolt, H., *CT–Guided "Real Time" Stereotaxy*, ACTA Neurochirurgica, 1989.

Roberts, D.W., Strohbehn, J.W., Hatch, J.F., Murray, W., Kettenberger, H., *A frameless stereotaxic integration of computerized tomographic imaging and the operating microscope*, J. Neurosurg., vol. 65, Oct. 1986, pp. 545–549.

Rosenbaum, A.E., Lunsford, L.D., Perry, J.H., *Computerized Tomography Guided Sterotaxis: A New Approach*, Applied Neurophysiology, vol. 43, No. 3–5, 1980, pp. 172–173.

Sautot, Pascal Phillippe, "Vissage Pediculaire Assiste Par Ordinateur," Sep. 20, 1994.

Selvik, G., et al., "A Roentgen Stereophotogrammetric System," Acta Radiologica Diagnosis, 1983, pp. 343–352.

Shelden, C.H., McCann, G., Jacques, S., Lutes, H.R., Frazier, R.E., Katz, R., Kuki, R., *Development of a computerized microstereotaxic method for localization and removal of minute CNS lesions under direct 3–D vision*, J. Neurosurg., vol. 52, 1980, pp. 21–27.

Smith, K.R., Bucholz, R.D., *Computer Methods for Improved Diagnostic Image Display Applied to Stereotactic Neurosurgery*, Automedical, vol. 14, 1992, pp. 371–382.

Viant, W.J., et al., "A Computer Assisted Orthopaedic System for Distal Locking of Intramedullary Nails," Proc. of MediMEC '95, Bristol, 1995, pp. 86–91.

Watanabe, E., Watanabe, T., Manaka, S., Mayanagi, Y., Takakura, K., *Three–Dimensional Digitizer (Neuronavigator): New Equipment for Computed Tomography–Guided Stereotaxic Surgery*, Surgical Neurology, vol. 27, No. 6, Jun. 1987, pp. 543–547.

Watanabe, H., *Neuronavigator*, Igaku–no–Ayumi, vol. 137, No. 6, May 10, 1986, pp. 1–4.

Weese, Jürgen, et al., "An Approach to 2D/3D Registration of a Vertebra in 2D X–ray Fluoroscopies with 3D CT Images," pp. 119–128.

\* cited by examiner

FLUOROSCOPIC IMAGE GUIDED ORTHOPAEDIC SURGERY SYSTEM WITH INTRAOPERATIVE REGISTRATION

CROSS REFERENCE TO RELATED APPLICATIONS

This application claims the benefit under 35 U.S.C. § 119 of U.S. Provisional Patent Application Serial No. 60/097,742 entitled "Fluoroscopic Image Guided Orthopaedic Surgery System with Intraoperative Registration" and having a filing date of Aug. 24, 1998 and U.S. Provisional Patent Application Serial No. 60/097,183 entitled "Fluoroscopic Image Guided Orthopaedic Surgery System with Intraoperative Registration" and having a filing date of Aug. 20, 1998.

BACKGROUND OF THE INVENTION

In orthopaedic surgery it is often necessary to insert a guide pin for a cannulated screw, drill bit, or other screw (hereafter referred to as a fixation device) into a bone at a predetermined trajectory. Pre-operative planning depends on two-dimensional radiographic images which typically consist of two views taken at approximately right angles to one another. From these two views it is possible to determine the shape and structure of a long bone. Using that method, the path of insertion for a guide pin for a cannulated screw, drill bit, or screw is accurately determined. However, in practice the actual aiming of a fixation device is an inaccurate art, as the object bone is often seen only at one surface or is not seen at all and, therefore, positioning is dependent on fluoroscopic visualization. This method is also time consuming as the C-arm images must be taken separately and the drapes must be rearranged each time an image is taken. As bony tissue is unyielding, the track of the pin or drill bit is determined by the angular approach before entering the object bone. This angular approach is difficult to determine under normal circumstances and often multiple attempts are needed, as feedback is obtained from repeated fluoroscopic images. Existing methods of calculating the proper angle of guide pin for a cannulated hip screw insertion for hip pinning involve placing data manually into a computer program, which in turn outputs an angle of guide pin for a cannulated hip screw insertion.

Radiation exposure is a necessary part of any procedure for calculating the proper angle of a guide pin, drill bit, or screw insertion. Radiation exposure is considered to be a hazard. Ionizing radiation has no safe threshold of exposure below which it ceases to have adverse effects, although an arbitrary level is assumed. There has been a recent upward revision of risk estimates of radiation exposure, but absolute levels of safe exposure remain unknown. Exposure to the surgical team as well as the patient during orthopaedic procedures using fluoroscopy is a universal concern. Consequently, a reduction in the amount of radiation exposure is highly desirable.

Operative stereotactic localization using either frames or three-dimensional digitizers is currently being used in neurosurgery or otoloaryngology. Those methods require the use of computed axial tomography (CT) or magnetic resonance imaging (MRI) prior to surgery. They also involve placing markers on the scalp prior to the imaging study of the head. The markers must be left in the same position until surgery is performed in order to confirm intraoperative registration. Such imaging studies are routinely performed for most intracranial procedures but are impractical for most orthopaedic procedures, especially those involving long bones. A probe marked with light emitting diodes (LEDs) or other digitizing emitters is used to localize these markers or pins using a three-dimensional digitizing device at the time of surgery. A disadvantage of this system is that the images are normally obtained hours before use; thus, the images used are not up to date (real time) and are often not reflective of the current condition of the object bone.

Registration markers cannot be used on the outside of the body in most orthopaedic cases as the skin does not adhere to the underlying bone. Pre-operative registration for robotic placement of the femoral components for total hip arthroplasty requires the use of a separate procedure to insert screws for such markers. Such a separate procedure is highly impractical for routine orthopaedic procedures.

An alternative method of registration for image guided surgery requires wide operative exposure, such as in pedicle screw insertion in spine surgery. The various fiducials are determined by touching prominent or distinctive anatomic points with a digitizing probe as employed by the stereotactic localization system. Furthermore, the system also requires preoperative computed axial tomography.

A system using fluoroscopic images to guide the insertion of a fixation device employs tracking with a three-dimensional optical digitizer. This optical digitizer is used to determine the position in six degrees of freedom of a portable fluoroscopy machine ("C-arm fluoroscope") and the object region of the skeleton. Light emitting diodes ("LEDs") are placed in distinctive patterns on the C-arm. Another set of LEDs are attached to the bone with a percutaneous screw device, such as a reference bar. A computer program records these positions in relation to an optical position sensor.

X-rays are then taken with the C-arm fluoroscope with the two positions of the tube at approximate right angles to one another. The optical position sensor can thus determine where the C-arm is positioned in relation to LED markers attached to the reference bar attached to the object section of the skeleton. The exact position is determined by using two-dimensional image registration, matching the outline of the bone in two planes. In this system, three or more distinctly shaped radiographic markers are attached to threaded tipped registration pins inserted percutaneously. Thus, the object portion of the skeleton is localized in six degrees of freedom by the optical digitizer.

The computer program relates the position of the object bone with or without fiducial markers in the two fields to determine the exact relative position of the object bone seen on the two images. Once those two images are displayed on monitors, no further x-rays are needed. Thus, a substantial reduction in the amount of ionizing radiation results. The images displayed are those familiar to the surgeon but with the usual distortion eliminated.

A drill with attached LEDs inserts the fixation device in the position in the bone that the surgeon chooses based on the supplied information. The three-dimensional optical digitizer determines the position of the drill in relation to the optical digitizer camera and the object section of the skeleton with its fiducials. A graphic display of the fixation device of predetermined length is then overlaid on the images of the object bone in near real time. Thus, the position of the inserted pin or drill bit can be adjusted immediately.

SUMMARY OF THE INVENTION

The present invention allows an orthopaedic surgeon to safely determine the precise trajectory of insertion of a fixation device into an object bone and to check the accuracy of the procedure using real time feedback.

The same three-dimensional optical digitizer is used to determine the position in six degrees of freedom of a portable fluoroscopy machine (C-arm fluoroscope) and the object regional of the skeleton. Light emitting diodes (LEDs) are placed in distinctive patterns on the C-arm and attached to the bone, the latter with a percutaneous screw device, such as a reference bar. A computer program records these positions in relation to an optical position sensor.

X-rays are then taken with the C-arm fluoroscope with the two positions of the tube at approximate right angles to one another. The optical position sensor can thus determine where the C-arm is positioned in relation to LED markers attached to the reference bar attached to the object section of the skeleton. The exact position is determined by using two-dimensional image registration, matching the outline of the bone in two planes.

In this invention, distinctly shaped radiographic markers are not required to match the position of the object bone with the image thereof. Matching, or registration, is performed by a single registration pin or other object that is seen on both x-ray views. The spherical shape of the femoral head may be used to increase the accuracy of the registration if the invention is used for hip surgery. When used for inserting distal locking screws for intramedullary nails, the presence of the nail alone with the holes for the interlocking screws can be used as fiducial reference marker. This method of image registration is clearly superior to the use of three special registration pins with specialized markers.

The fixation device can then be inserted using a drill or drill guide that has attached LEDs that serve as means to localize it in six degrees of freedom. The graphic representation of the guide pin for a cannulated screw, drill bit, or extended projection of the drill guide positioned appropriately on the pair of monitors can be used to determine the correct trajectory.

Accurate localization of a hip screw in the femoral head has been shown in an important clinical study to result in much superior results than if the screw is placed eccentrically. Accurate aiming of an interlocking screw in an intramedully nail is difficult to obtain using all current techniques. It is improved by this invention such that operative time and radiation are markedly reduced.

This invention has the advantage of simplifying the operation and making it more acceptable to use computer assisted surgery to improve accuracy.

DESCRIPTION OF THE PREFERRED EMBODIMENTS

Figure 1:
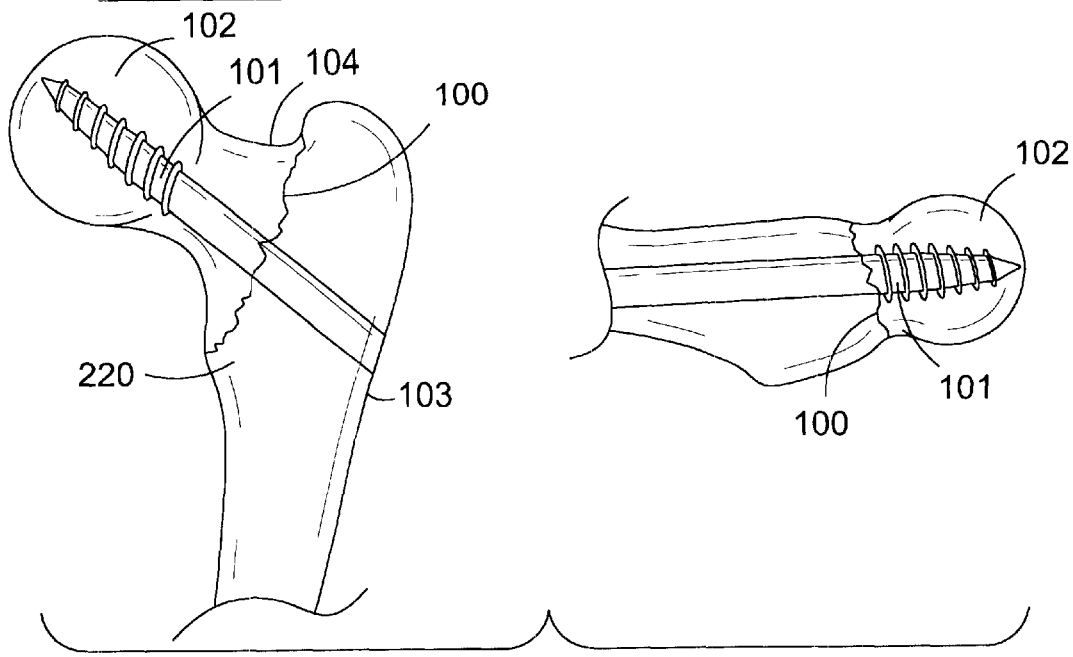
FIG. 1 is an illustration of anterior and lateral x-ray views of the proximal femur with an intertrochanteric fracture with a hip screw in optimal position.
Figure 2A:
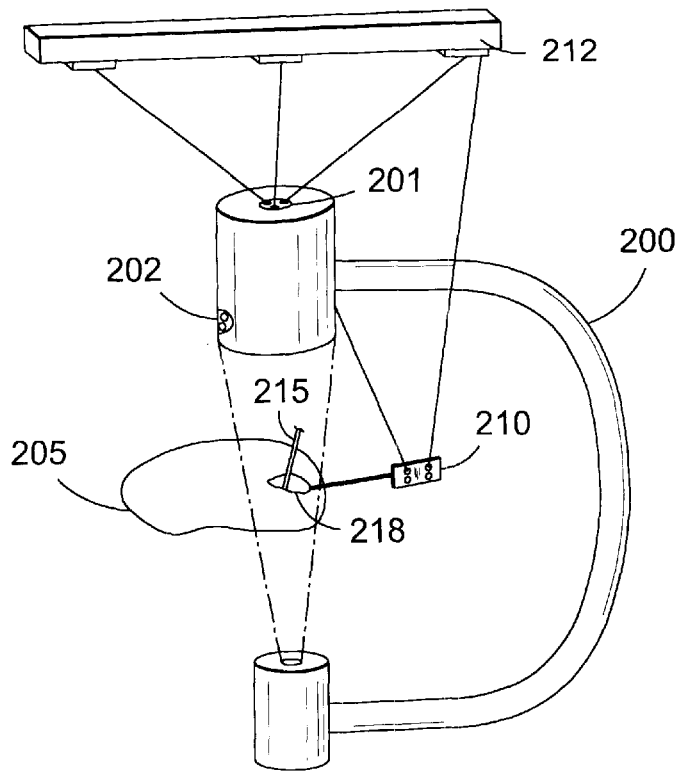
FIGS. 2A & 2B are perspective illustrations of the intraoperative setting showing the C-arm fluoroscope, an optical digitizer camera, and the object body.
Figure 2B:
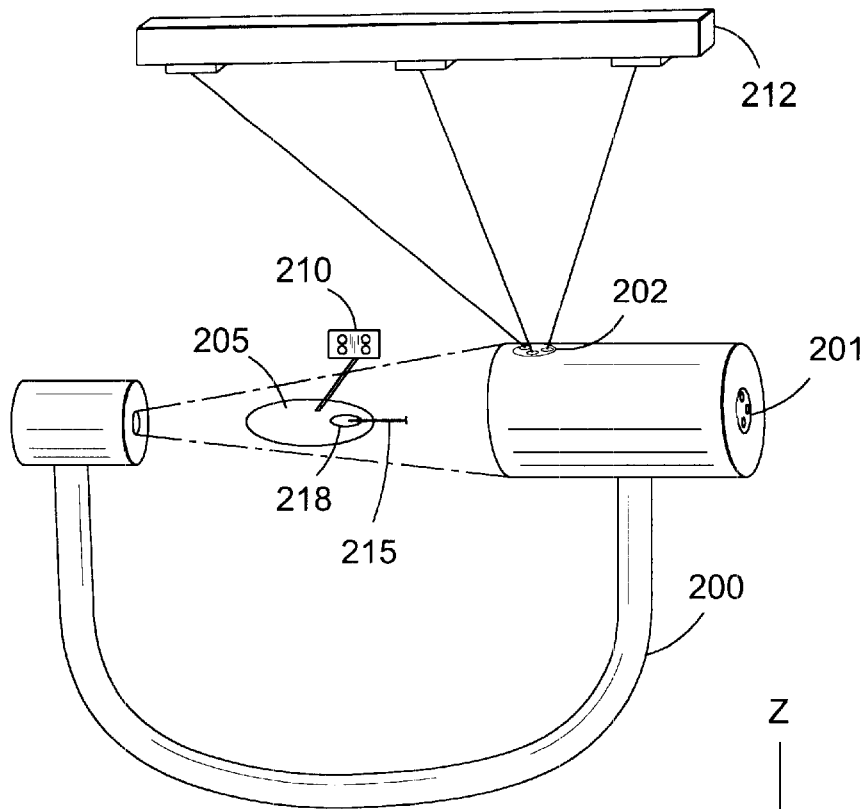
Figure 4:
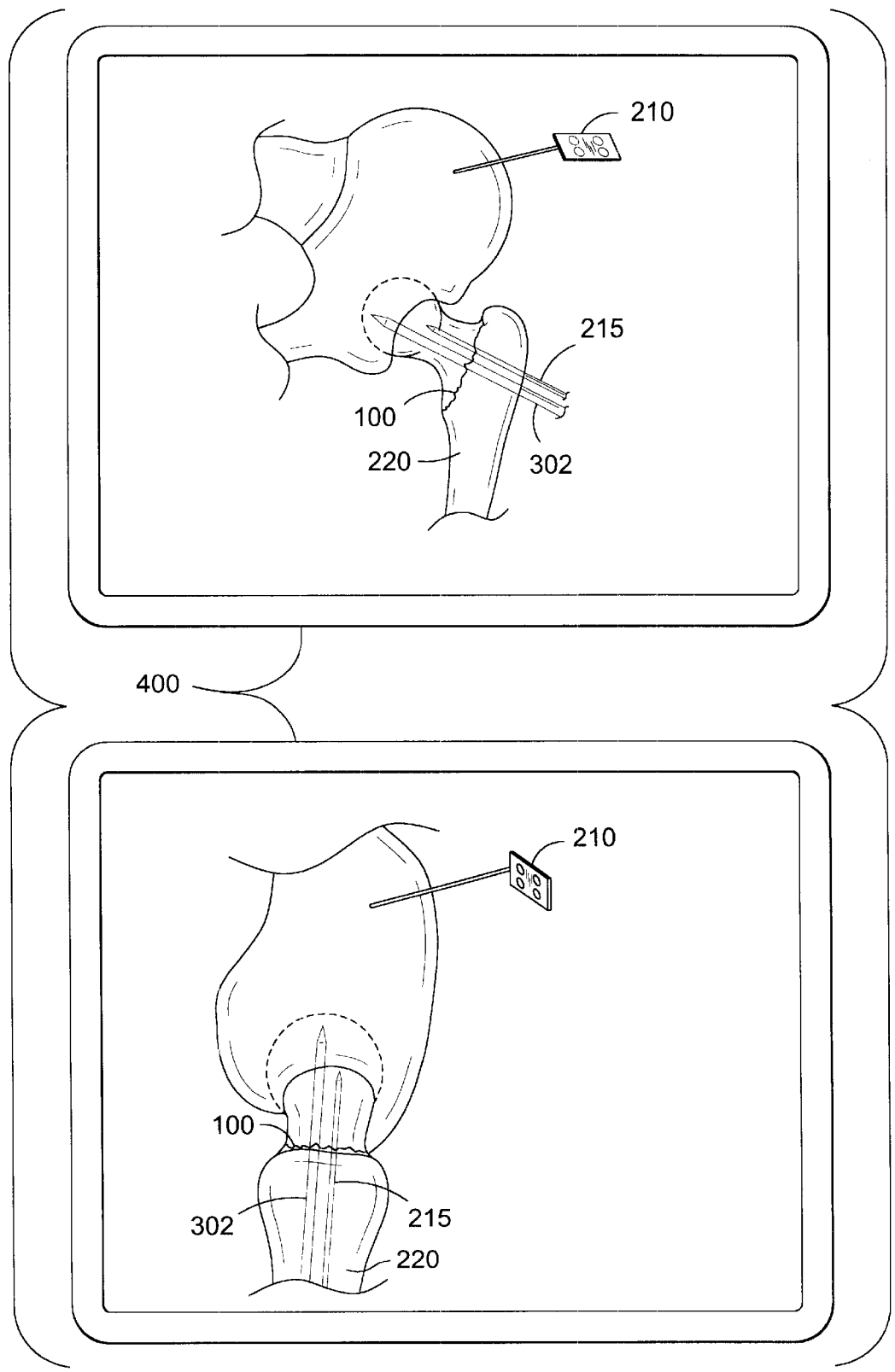
FIG. 4 is an illustration of a pair of computer monitor screens with radiographic images of the object bone at positions approximately 90 degrees to one another, with a single registration pin and a reference bar in place, and with the graphic image of a guide pin 302 for a cannulated hip screw superimposed.

The operation for the internal fixation of intertrochanteric hip fracture 100 requires a guide pin for a cannulated hip screw, and subsequently cannulated screw 101, to be placed into femoral head 102 from lateral cortex 103 of proximal femur 220 via femoral neck 104, as illustrated in FIG. 1. Guide pin 302 for cannulated hip screw 101 determines the position of cannulated screw 101. The ideal position of the guide pin for a cannulated hip screw, and thus screw 101, is entirely within bone. The end of the pin, and screw 101, is best positioned very near the subcortical bone but should not penetrate the cortex and thus enter the hip joint. The best results of an intertrochanteric fracture 100 must have been shown to occur when large screw 101 used is in the center of the femoral head at the subcortical bone. This position is normally obtained by placing the guide pin for a cannulated hip screw by estimation and by following its course on entry with repeated x-rays views in two planes. C-arm fluoroscope 200, as seen in FIG. 2, must be moved from one position of the other. Repeated attempts may be needed before the optimal position of guide pin 302, as seen in FIG. 4, for a cannulated hip screw can be obtained. Operating time and radiation exposure would be reduced by using image guided surgery. The accuracy and thus long term results would be improved.

In this system of fluoroscopic image guided orthopaedic surgery with intraoperative registration, light emitting diodes (LEDs) are attached to portable C-arm fluoroscopy 200 at two sites. One LED 201 is placed to determine the position of C-arm 200 when in the upright position as in FIG. 2A, which corresponds to the anteroposterior x-ray view when the patient 205 is supine. Another LED 202 is located so that it is seen by optical digitizer camera 212 when C-arm 200 is horizontal as in FIG. 2B, corresponding to the lateral x-ray view.

Patient 205 is lying supine in traction on a fracture table during the procedure. After appropriate sterile preparation, reference bar 210 with LEDs is inserted through a small incision into ilium 218. The optical digitizer software is programmed to recognize the region of the skeleton attached to reference bar 210 as a rigid body. The rigid body computer model thus remains immobile, and the other objects with LEDs attached move in relation to this rigid body. Femur 220 must remain immobile in relation to ilium 218, which is usually the case. FIG. 4 illustrates x-ray views seen with the fluoroscope.

Then proximal femur 220 is exposed through a routine lateral incision. Registration pin 215 is then inserted in proximal femur 220. X-rays at approximate right angles are then taken in the standard anteroposterior and lateral views. When C-arm 200 is in the upright position (FIG. 2A), LEDs 201 facing optical digitizer camera 212 indicate to the computer where C-arm 200 is in three dimensional space. Thus the computer can calculate the plane in which body 205 lies—in relation to reference bar 210. When C-arm 200 is in the horizontal position (FIG. 2B), LEDs 202 are now facing optical digitizer camera 212 and indicate again where C-arm 200 is in three dimensional space when in this position. The computer can then calculate exactly where body 205 and femur 220 seen on x-ray are in relation to optical digitizer camera 212. This calculation is possible with registration pin 215 and femur 220 now being recorded in two positions. The method of finding the position of registration pin 215 is a type of image registration.

Figure 3:
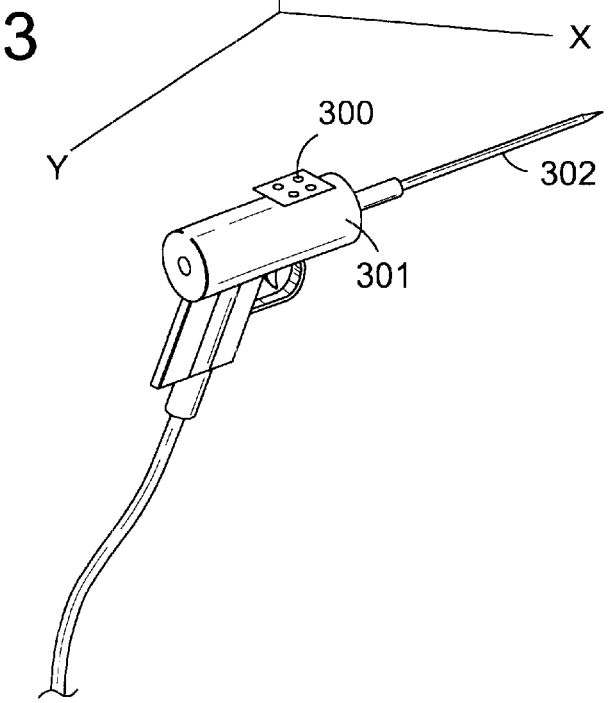
FIG. 3 is an illustration of a drill with mounted light emitting diodes.

LEDs 300 are mounted on the body of drill 301 as shown in FIG. 3. Guide pin 302 for cannulated hip screw 101 is placed in position into drill 301.

The signals emitted from LEDs 300 on drill 301 are received by optical digitizer camera 212 when placed in the operating field. the computer can then determine the position of drill 301 to reference bar 210 and thus to femur 220. A graphic image of guide pin 302 for a cannulated hip screw can then be displayed on each monitor 400 as seen in FIG. 4 to show the relationship of guide pin 302 for a cannulated hip screw to femur 220 in both the anteroposterior and the lateral views. Guide pin 302 for cannulated hip screw 101 can then be inserted in the desired position with image guidance.

If reference bar 210 should be moved or loosened, registration can be done again during the operation just be repeating the two x-ray views. Once registration pin 215 is in place, identification of fiducials by the tedious method of touching points with a probe is unnecessary. The accuracy of image registration with registration pin 215 or other object is much greater than with previous methods.

What is claimed is:

1. A fluoroscopic image guided surgery system comprising:
   a C-arm fluoroscope for obtaining fluoroscopic images of an object bone, the C-arm fluoroscope including at least one set of radiators;
   a reference bar capable of attaching to the object bone, the reference bar including radiators;
   a surgical instrument for performing an operation, the instrument including radiators;
   a position sensor capable of sensing the at least one set of radiators of the C-arm fluoroscope, the radiators of Fe reference bar, and the radiators of the surgical instrument so that the position sensor can determine a position of at least one of the C-arm fluoroscope and the surgical instrument with respect to the reference bar; and
   only one fiducial marker for attachment to the object bone, the one fiducial marker and a shape of the object bone being visible in the fluoroscopic images wherein only the one fiducial marker and the shape of the object bone are used for determining a position of the object bone relative to the position sensor.

2. The system of claim 1, wherein the radiators are emitters.

3. The system of claim 1, wherein the radiators are LED emitters.

4. The system of claim 1, wherein the C-arm fluoroscope comprises an x-ray generator and an x-ray receiver.

5. The system of claim 1, further comprising a computer program for determining a plane in which a patient body lies in relation to the reference bar.

6. The system of claim 1, wherein the at least one set of radiators of the C-arm fluoroscope comprises two sets of radiators.

7. The system of claim 1, wherein the position sensor comprises a digitizer system.

8. The system of claim 7, wherein the digitizer system comprises an optical digitizer camera.

9. A fluoroscopic image guided surgery system, comprising:
   a fluoroscopic imager for generating an image of a region of a patient, at least one radiator being positioned on the fluoroscopic imager;
   a surgical instrument capable of being positioned proximate the region, at least one radiator being positioned on the surgical instrument;
   a reference device capable of positioning In the region of the patient, at least one radiator being positioned in the reference device:
   a position sensor for sensing signals emitted by radiators of the fluoroscopic Imager, the surgical Instrument, and the reference device, and for determining positions of at least one of the fluoroscopic imager and the surgical instrument with respect to the reference device;
   only one fiducial marker for attachment to the region, the one fiducial marker and a shape of the region being visible in the fluoroscopic images, wherein only the one fiducial marker and the shape of the region are used for determining a position of the region relative to the position sensor; and
   a monitor for displaying the image of the region produced by the fluoroscopic imager and the position of the surgical instrument overlaying the image in near real time for continually monitoring a position of the surgical instrument.

10. The system of claim 9, wherein the radiators are emitters.

11. The system of claim 9, wherein the radiators are LED emitters.

12. The system of claim 9, wherein the position sensor comprises a digitizer system.

13. The system of claim 12, further comprising a computer programmed to match images from the fluoroscope image to effect a two-dimensional image registration.

14. The system of claim 9, further comprising a computer programmed to match images from the fluoroscopic imager to effect a two-dimensional image registration.

15. The system of claim 9, wherein the fluoroscopic imager is a C-arm fluoroscope.

16. A method of performing fluoroscopic image guided surgery with Intraoperative registration, comprising the steps of:
   attaching a reference device to an object bone in a region of a patient, the reference device having a first set of radiators;
   obtaining at least one fluoroscopic image of the region, the Image being obtained by a fluoroscopic imager having a second set of radiators;
   determining a position of the fluoroscopic imager relative to the reference device for the at least one fluoroscopic Image by detecting signals from the first and second set of radiators using a position sensor;
   storing the at least one fluoroscopic image and the fluoroscopic imager position;
   placing a surgical instrument proximate to the region, the surgical Instrument having a third set of radiators;
   determining a position of the surgical instrument relative to the reference device by detecting signals from the first and third set of radiators using a position sensor;
   attaching only one fiducial marker to the object bone;
   determining a position of the object bone relative to the position sensor by use of only the one fiducial marker and a shape of the object bone; and
   real-time displaying the at least one fluoroscopic image with an image of the surgical instrument.

17. The method of claim 16, further comprising:
   using a C-arm fluoroscope to obtain the at least one fluoroscopic image of the region.

18. The method of claim 16, wherein using the first, second, and third sets of radiators includes using emitters as the first, second and third sets of radiators.

19. The method of claim 16, wherein using the first, second, and third sets of radiators includes using LED emitters as the first, second and third sets of radiators.

20. The method of claim 16, wherein the steps of determining a position comprise a step of using an optical position sensor.

21. The method of claim 20, wherein using the optical position sensor includes using a digitizer system.

22. The method of claim 21, wherein using the digitizer system includes using a digitizer camera.

23. A fluoroscopic image guided surgery system, comprising:

a C-arm fluoroscope for obtaining fluoroscopic Images of an object bone, the C-arm fluoroscope including at least one set of emitters;

a reference bar capable of attaching to the object bone, the reference bar including emitters;

a surgical instrument for performing an operation, the instrument including emitters:

a digitizer system In communication with the at least one set of emitters of the C-arm fluoroscope, the emitters of the reference bar, and the emitters of the surgical instrument so that the digitizer system can determine a position of each of the C-arm fluoroscope, the reference bar, and the surgical Instrument; and only one fiducial marker for attachment to the object bone, the one fiducial marker being visible in the fluoroscopic images, wherein only the one fiducial marker and a shape of the object bone are used for determining a position of the object bone relative to the digitizer system.

\* \* \* \* \*

UNITED STATES PATENT AND TRADEMARK OFFICE
CERTIFICATE OF CORRECTION

PATENT NO.    : 6,477,400 B1
DATED         : November 5, 2002
INVENTOR(S)   : Earl Frederick Barrick It is certified that error appears in the above-identified patent and that said Letters Patent is hereby corrected as shown below:

Column 4,
Line 16, "of" should read -- to --.

Column 5,
Line 11, "be" (second occurrence) should be -- by --.
Line 29, delete "Fe".
Line 65, "In" should be -- in --.

Column 6,
Line 2, "Imager" should be -- imager --.
Line 2, "Instrument" should be -- instrument --.
Line 34, "Intraoperative" should be -- intraoperative --.
Lines 41 and 45, "Image" should be -- image --.
Line 51, "Instrument" should be -- instrument --.

Column 7,
Line 13, "Images" should be -- images --.

Column 8,
Line 3, "In" should be -- in --.

Signed and Sealed this

Sixth Day of January, 2004

JAMES E. ROGAN
*Director of the United States Patent and Trademark Office*